United States Patent
Hamasaki et al.

(10) Patent No.: US 7,476,760 B2
(45) Date of Patent: Jan. 13, 2009

(54) PURIFICATION AND PRODUCTION METHODS OF 1-AMINOCYCLOPROPANECARBOXYLIC ACID

(75) Inventors: Ryota Hamasaki, Tsukuba (JP); Mitsuru Ohno, Tsukuba (JP)

(73) Assignee: Daicel Chemical Industries, Ltd., Sakai (JP)

(*) Notice: Subject to any disclaimer, the term of this patent is extended or adjusted under 35 U.S.C. 154(b) by 573 days.

(21) Appl. No.: 11/183,858

(22) Filed: Jul. 19, 2005

(65) Prior Publication Data
US 2006/0030730 A1    Feb. 9, 2006

(30) Foreign Application Priority Data
Aug. 5, 2004    (JP)    ............................ 2004-229872

(51) Int. Cl.
*C07C 62/00*    (2006.01)
(52) U.S. Cl. ...................................... 562/506
(58) Field of Classification Search .................. None
See application file for complete search history.

(56) References Cited

U.S. PATENT DOCUMENTS
5,569,781 A * 10/1996 Kleemiss et al. ............ 562/506

FOREIGN PATENT DOCUMENTS
JP    7-278077 A    10/1995

OTHER PUBLICATIONS
J. Am. Chem. Soc., vol. 106, No. 18, 1984, pp. 5335-5348.
J. Org. Chem., vol. 54, 1989, pp. 1810-1815.
J. Org. Chem., vol. 55, 1990, pp. 4276-4281.

* cited by examiner

*Primary Examiner*—Paul A Zucker
(74) *Attorney, Agent, or Firm*—Birch, Stewart, Kolasch & Birch, LLP

(57) ABSTRACT

A method purifies 1-aminocyclopropanecarboxylic acid by subjecting a crude 1-aminocyclopropanecarboxylic acid to crystallization with a solvent mixture containing an organic acid having one to five carbon atoms and a poor solvent for 1-aminocyclopropanecarboxylic acid, which poor solvent is miscible with the organic acid. In the method, the solvent mixture may further contain water. Purification may be carried out by mixing the crude 1-aminocyclopropanecarboxylic acid with the organic acid having one to five carbon atoms, removing insoluble matter by filtration, and adding the poor solvent with or without water to the filtrate to thereby crystallize 1-aminocyclopropanecarboxylic acid.

5 Claims, No Drawings

PURIFICATION AND PRODUCTION METHODS OF 1-AMINOCYCLOPROPANECARBOXYLIC ACID

BACKGROUND OF THE INVENTION

1. Field of the Invention

The present invention relates to a purification method and production method of 1-aminocyclopropanecarboxylic acid that is useful typically as an intermediate for fine chemicals such as pharmaceutical preparations and agricultural chemicals.

2. Description of the Related Art

1-Aminocyclopropanecarboxylic acid is useful typically as an intermediate for fine chemicals such as pharmaceutical preparations and agricultural chemicals and can be prepared by allowing 1-carbamoylcyclopropanecarboxylic acid to react with an aqueous sodium hydroxide solution and a bromine reagent (J. Am. Chem. Soc., 1984, 106, 5335-5348).

1-Aminocyclopropanecarboxylic acid is purified, for example, a purification method by ion-exchange column chromatography (J. Am. Chem. Soc., 1984, 106, 5335-5348); a method of mixing 1-aminocyclopropanecarboxylate hydrochloride with propylene oxide in ethanol solvent with stirring to thereby yield free 1-aminocyclopropanecarboxylic acid, concentrating the reaction mixture to dryness, and crystallizing the crude product from a mixture of water and acetone (J. Org. Chem., 1989, 1810-1815); a method of mixing 1-aminocyclopropanecarboxylate hydrochloride with potassium carbonate in methanol solvent with stirring to thereby yield free 1-aminocyclopropanecarboxylic acid, removing insoluble matter by filtration, concentrating the filtrate to dryness, and recrysltallizing the target compound from a mixture of ammonium hydroxide and ethanol (J. Org. Chem., 1990, 4276-4281); or a method of treating a reaction mixture containing 1-aminocyclopropanecarboxylic acid with hydrochloric acid, evaporating the treated reaction mixture to dryness, and extracting, with ethanol, the target compound as a hydrochloride from a mixture containing an inorganic salt (Japanese Unexamined Patent Application Publication No. 07-278077).

However, the method using ion-exchange column chromatography requires concentration of a large quantity of water, requires much time for separation, must be carried out using special devices and is not advantageous in industrial production. The method using propylene oxide is not industrially advantageous, since propylene oxide itself is very flammable, is spontaneously explosive and is hard to handle industrially. The method of crystallizing the target compound from a mixture of water and acetone cannot yield the target compound with high quality in a good yield, since the target compound 1-aminocyclopropanecarboxylic acid has a similar solubility to that of, if in coexistence, an inorganic salt such as sodium chloride or sodium bromide. The method of mixing 1-aminocyclopropanecarboxylate hydrochloride with potassium carbonate in methanol solvent with stirring to thereby yield free 1-aminocyclopropanecarboxylic acid, removing insoluble matter by filtration, concentrating the filtrate to dryness, and recrysltallizing the target compound from a mixture of ammonium hydroxide and ethanol is complicated in its procedure and is not industrially advantageous, since 1-aminocyclopropanecarboxylic acid is hardly soluble in methanol with a very low solubility of about 1.0% (wt/wt) and a large quantity of methanol is required. The method of extracting 1-aminocyclopropanecarboxylic acid as a hydrochloride with ethanol requires removal of hydrochloric acid before a subsequent process, which invites an increasing number of processes.

SUMMARY OF THE INVENTION

Accordingly, an object of the present invention is to provide methods for industrially efficiently purifying and producing 1-aminocyclopropanecarboxylic acid.

After intensive investigations to achieve the above objects, the present inventors have found that 1-aminocyclopropanecarboxylic acid is efficiently crystallized to yield high-purity 1-aminocyclopropanecarboxylic acid with good productivity by using, as a crystallization solvent, an organic acid having one to five carbon atoms in combination with a poor solvent for 1-aminocyclopropanecarboxylic acid, and where necessary, further with water; 1-aminocyclopropanecarboxylic acid is efficiently purified by adding an organic acid having one to five carbon atoms to crude 1-aminocyclopropanecarboxylic acid to thereby efficiently remove an inorganic substance by filtration, adding a poor solvent for the filtrate, and carrying out crystallization, since 1-aminocyclopropanecarboxylic acid is highly soluble in such an organic acid having one to five carbon atoms but the inorganic substance such as sodium chloride or sodium bromide formed in the production reaction of 1-aminocyclopropanecarboxylic acid is hardly soluble in the organic acid. In addition, they found that this purification method is suitable as a final process in industrial production of 1-aminocyclopropanecarboxylic acid. The present invention has been achieved based on these findings.

Specifically, the present invention provides, in an aspect, a method for purifying 1-aminocyclopropanecarboxylic acid, including the step of subjecting a crude 1-aminocyclopropanecarboxylic acid to crystallization with a solvent mixture containing an organic acid and a poor solvent for 1-aminocyclopropanecarboxylic acid, the organic acid having one to five carbon atoms, and the poor solvent being miscible with the organic acid.

In the purification method, the solvent mixture may further contain water. The method may include the steps of mixing the crude 1-aminocyclopropanecarboxylic acid with the organic acid having one to five carbon atoms, removing insoluble matter by filtration, and adding the poor solvent with or without water to the filtrate to thereby crystallize 1-aminocyclopropanecarboxylic acid. The organic acid is preferably acetic acid, and the poor solvent is preferably ethanol.

The present invention further provides, in another aspect, a method for producing 1-aminocyclopropanecarboxylic acid, including the step of purifying a reaction product by the above-mentioned purification method, the reaction product being yielded by converting 1-carbamoylcyclopropanecarboxylic acid to 1-aminocyclopropanecarboxylic acid.

The present invention can efficiently purify 1-aminocyclopropanecarboxylic acid not as a salt but as a free compound in short processes without using extra devices and/or hard-to-handle compounds and is industrially very advantageous.

Further objects, features and advantages of the present invention will become apparent from the following description of the preferred embodiments.

DESCRIPTION OF THE PREFERRED EMBODIMENT

According to the present invention, crude 1-aminocyclopropanecarboxylic acid is subjected to crystallization using a solvent mixture comprising an organic acid and a poor solvent for 1-aminocyclopropanecarboxylic acid, which organic acid has one to five carbon atoms, and which poor solvent is miscible with the organic acid. The solvent mixture may further contain water.

1-Aminocyclopropanecarboxylic acid can be synthetically prepared according to a conventional procedure. For example, it can be induced from 1-carbamoylcyclopropanecarboxylic acid by the method described in J. Am. Chem. Soc., 1984, 106, 5335-5348 (Hofmann rearrangement). In the method of the present invention, a crude 1-aminocyclopropanecarboxylic acid to be subjected to purification is not specifically limited regardless of its obtaining method such as the type of reaction and/or a treating procedure thereafter. The crude 1-aminocyclopropanecarboxylic acid to be purified may be formed by subjecting the reaction mixture to a necessary treatment such as adjustment of pH, and concentrating the treated mixture and may contain, for example, an inorganic salt. Alternatively, the crude 1-aminocyclopropanecarboxylic acid may be further subjected to filtration so as to remove such an inorganic acid and other impurities to some extent before purification.

Examples of the organic acid having one to five carbon atoms for use in the present invention are carboxylic acids each having one to five carbon atoms, such as formic acid, acetic acid, propionic acid and trifluoroacetic acid. Each of these organic acids can be used alone or in combination. The organic acid is preferably an organic acid having one to three carbon atoms, and is more preferably acetic acid.

The amount of the organic acid having one to five carbon atoms for use in crystallization of 1-aminocyclopropanecarboxylic acid is generally from about 1 to about 50 parts by weight, and preferably from about 5 to about 10 parts by weight to 1 part by weight of 1-aminocyclopropanecarboxylic acid contained in the crude 1-aminocyclopropanecarboxylic acid, while it varies depending typically on the type and amount of impurities contained in the crude 1-aminocyclopropanecarboxylic acid and the amount of the poor solvent.

The poor solvent for 1-aminocyclopropanecarboxylic acid which is miscible with the organic acid having one to five carbon atoms includes solvents miscible with the organic acid in the coexistence of water and solvents miscible with the organic acid in the absence of water. The "poor solvent" as used herein means a solvent in which 1-aminocyclopropanecarboxylic acid has a low solubility, such as a solvent in which 1-aminocyclopropanecarboxylic acid has a solubility of 8.0 g or less per 100 g at ordinary temperature.

Examples of the solvents miscible with the organic acid in the coexistence of water are ketone solvents such as acetone and ethyl methyl ketone; amide solvents such as N,N-dimethylformamide and N,N-dimethylacetamide; and alcohol solvents such as methanol, ethanol, and 2-propanol. Examples of the solvents miscible with the organic acid in the absence of water are ester solvents such as methyl acetate and ethyl acetate; ether solvents such as t-butyl methyl ether, diisopropyl ether, and tetrahydrofuran; nitrile solvents such as acetonitrile and benzonitrile; aliphatic hydrocarbon solvents such as hexane and heptane; aromatic hydrocarbon solvents such as benzene and toluene; halogen-containing solvents such as dichloromethane, 1,2-dichloroethane, and chlorobenzene; ketone solvents such as acetone and ethyl methyl ketone; amide solvents such as N,N-dimethylformamide and N,N-dimethylacetamide; and alcohol solvents such as methanol, ethanol, and 2-propanol. Each of these poor solvents can be used alone or in combination. Of these poor solvents, alcohol solvents are preferred from the viewpoints of crystallization yield and purity, of which ethanol is typically preferred.

The amount of the poor solvent can be set suitably so as to enable crystallization of the target compound 1-aminocyclopropanecarboxylic acid. The optimum amount of the poor solvent varies depending typically on the route for obtaining the crude 1-aminocyclopropanecarboxylic acid (crude fraction) to be purified. In purification of a reaction product as a result of conversion of 1-carbamoylcyclopropanecarboxylic acid to 1-aminocyclopropanecarboxylic acid, for example, the amount of the poor solvent is generally from about 1 to about 100 parts by weight, and preferably from about 5 to about 30 parts by weight, to 1 part by weight of the starting compound 1-carbamoylcyclopropanecarboxylic acid. The amount of the poor solvent is, for example, from about 1 to about 100 parts by weight, and preferably from about 5 to about 30 parts by weight, to 1 part by weight of 1-aminocyclopropanecarboxylic acid contained in the crude 1-aminocyclopropanecarboxylic acid.

When the crude 1-aminocyclopropanecarboxylic acid to be purified contains a substance insoluble in the organic acid having one to five carbon atoms, such as an inorganic acid including sodium chloride and sodium bromide, it is preferred (i) to carry out crystallization with a solvent mixture containing the organic acid having one to five carbon atoms, the poor solvent for 1-aminocyclopropanecarboxylic acid which is miscible with the organic acid, and water in which the inorganic salts are well soluble, or (ii) to mix the crude 1-aminocyclopropanecarboxylic acid with the organic acid having one to five carbon atoms, remove insoluble matter such as inorganic salts by filtration, and add the poor solvent with or without water to the filtrate to thereby crystallize 1-aminocyclopropanecarboxylic acid.

The amount of water, if used, can be suitably set within a range not adversely affecting the crystallization. The optimum amount of water varies depending on the route for obtaining the crude 1-aminocyclopropanecarboxylic acid. In purification of a reaction product as a result of conversion of 1-carbamoylcyclopropanecarboxylic acid to 1-aminocyclopropanecarboxylic acid, for example, the amount of water is generally preferably from about 0.01 to about 50 parts by weight, and more preferably from about 0.1 to about parts by weight, to 1 part by weight of the starting compound 1-carbamoylcyclopropanecarboxylic acid. The amount of water is, for example, from about 0.01 to 50 parts by weight, and preferably from about 0.1 to 5 parts by weight, to 1 part by weight of 1-aminocyclopropanecarboxylic acid contained in the crude 1-aminocyclopropanecarboxylic acid.

When insoluble matter such as an inorganic salt is removed by filtration in the procedure (ii), it is preferred to rinse filter cake with an organic acid having one to five carbon atoms.

The crystallization procedure is carried out at temperatures equal to or lower than the boiling point and equal to or higher than the melting point of the system. The crystallization temperature is generally from about −15° C. to about 70° C., preferably from about −10° C. to about 30° C., and more preferably from about −5° C. to about 10° C. If acetic acid and ethanol are used as the organic acid and the poor solvent, respectively, the crystallization temperature is most preferably set at temperatures from 0° C. to 5° C. The resulting 1-aminocyclopropanecarboxylic acid obtained by crystallization can be isolated typically by filtration and drying.

The resulting 1-aminocyclopropanecarboxylic acid can be used as an intermediate typically for fine chemicals such as pharmaceutical preparations and agricultural chemicals.

The present invention will be illustrated in further detail with reference to several examples and comparative examples below, which by no means limit the scope of the invention. NMR spectra were determined at 500 MHz ($^1$H-NMR) using BRUKER AM500. The purity of 1-aminocyclopropanecarboxylic acid was determined by high-performance liquid chromatography (HPLC) with a commercially available product as an authentic sample.

HPLC Condition

Column: Shodex RSpak NN-414, 150 mm×4.6 mm inside diameter

Mobile phase: $KH_2PO_4$ (pH 2.5 by $H_3PO_4$)/MeCN (acetonitrile) 50/50

Detection wavelength: UV (220 nm)

Detection temperature: 40° C.

Flow rate: 0.4 mL/min

Injection amount: 20 μL

Retention time: 9.88 min

Sample: 1000 ppm

EXAMPLE 1

To a stirred mixture of a 20 percent by weight aqueous sodium hydroxide solution (15.49 g, 77.5 mmol) and bromine (2.48 g, 15.5 mmol) was added 1-carbamoylcyclopropanecarboxylic acid (2.0 g, 15.5 mmol) under ice cooling. The reaction mixture after the completion of addition was heated to 40° C., followed by stirring for further four-and-half hours. The reaction mixture was adjusted to pH of 5.4 with concentrated hydrochloric acid under ice cooling, and the neutralized aqueous solution was concentrated to 9.99 g. The precipitate was filtrated, and the filter-cake was rinsed with acetic acid. The filtrate was concentrated to 9.98 g, the precipitate was filtrated, and the filter-cake was rinsed with acetic acid. The filtrate was again concentrated to 6.69 g, and the precipitate was removed by filtration. The filtrate was concentrated to 6.20 g, and ethanol (20 mL) was added thereto, followed by crystallization under ice cooling. The precipitated crystals were filtrated, were dried and thereby yielded 1-aminocyclopropanecarboxylic acid (yield: 0.95 g, percent yield: 61%, purity: 96.9%).

$^1$H-NMR ($D_2O$) δ: 1.05 (dd, 2H), 1.19 (dd, 2H)

EXAMPLE 2

Bromine (247.6 g, 1.55 mol) was added dropwise to a 20 percent by weight aqueous sodium hydroxide solution (1549.0 g, 7.75 mol) under ice cooling to thereby yield an aqueous sodium hypobromite solution. The resulting aqueous sodium hypobromite solution was added dropwise to a stirred mixture of 1-carbamoyl-cyclopropanecarboxylic acid (200 g, 1.55 mol) and water (400 mL) under ice cooling. After the completion of addition, the reaction mixture was heated to 40° C., followed by stirring for further eighteen hours. The reaction mixture was adjusted to pH of 5.5 with concentrated hydrochloric acid under ice cooling, and the neutralized aqueous solution was concentrated to 980 g, and acetic acid (800 mL) was added thereto, followed by concentration. After concentrating the reaction mixture to 1160 g, a precipitated inorganic salt was filtrated. The filter cake was rinsed with acetic acid (400 mL), and the filtrate was concentrated to 680 g. Water (76 g) was added to the concentrated filtrate, and the precipitated inorganic salt was heated and dissolved. Ethanol (4000 mL) was added to the mixture, followed by crystallization under ice cooling. The precipitated crystals were filtrated, were dried and thereby yielded 1-aminocyclopropanecarboxylic acid (yield: 104.0 g, percent yield: 66.4%, purity: 94.1%).

EXAMPLE 3

In acetic acid (1.6 mL) was dissolved 1-aminocyclopropanecarboxylic acid (0.200 g, purity: 98.6%) at room temperature. An organic solvent (2.0 mL) was added, and crystallization was carried out by stirring the mixture at room temperature for one hour. The precipitated crystals were filtrated, were dried and thereby yielded 1-aminocyclopropanecarboxylic acid. The percent yields in the cases of the following organic solvents are shown in Table 1.

TABLE 1

| Organic solvent | Percent yield (%) |
|---|---|
| Ethyl acetate | 88 |
| t-Butyl methyl ether | 75 |
| Acetonitrile | 70 |
| Hexane | 98 |
| Toluene | 90 |
| Dichloromethane | 63 |
| Acetone | 24 |
| N,N-Dimethylformamide | 57 |
| Ethanol | 58 |

EXAMPLE 4

In acetic acid (100 mL) was dissolved 1-aminocyclopropanecarboxylic acid (19.14 g, purity: 75.3%) at room temperature, followed by addition of water (20 mL). Ethanol (300 mL) was added to the stirred mixture, followed by crystallization under ice cooling. The precipitated crystals were filtrated, were dried and thereby yielded 1-aminocyclopropanecarboxylic acid (8.65 g, percent yield: 60%, purity: 98.6%).

COMPARATIVE EXAMPLE 1

To 1-carbamoylcyclopropanecarboxylic acid (1.0 g, 7.7 mmol) was added dropwise a 20 percent by weight aqueous sodium hydroxide solution (9.29 g, 46.2 mmol) under ice cooling. Next, bromine (1.49 g, 9.24 mmol) was added, and the reaction mixture was stirred at room temperature for sixteen hours, followed by stirring at 40° C. for further five-and-half hours. The reaction mixture was adjusted to pH of 1.0 with concentrated hydrochloric acid under ice cooling, but no 1-aminocyclopropanecarboxylic acid was precipitated.

COMPARATIVE EXAMPLE 2

Bromine (4.95 g, 31.0 mmol) was added dropwise to a 20 percent by weight aqueous sodium hydroxide solution (30.98 g, 155 mmol) under ice cooling to thereby yield an aqueous sodium hypobromite solution. The resulting aqueous sodium hypobromite solution was added dropwise to a stirred mixture of 1-carbamoylcyclopropanecarboxylic acid (4.0 g, 31.0 mmol) and water (8.0 mL) under ice cooling. After the completion of addition, the reaction mixture was heated to 40° C., followed by stirring for further fifteen hours. The reaction mixture under ice cooling was adjusted to pH of 5.7 with concentrated hydrochloric acid under ice cooling, and the neutralized aqueous solution was concentrated to 19.99 g. Ethanol (80 mL) was added thereto, followed by crystallization under ice cooling. The precipitated crystals were filtrated, were dried and thereby yielded 1-aminocyclopropanecarboxylic acid (yield: 0.61 g, percent yield: 20%, purity: 9.0%).

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for purifying 1-aminocyclopropanecarboxylic acid, comprising the step of subjecting a crude 1-aminocyclopropanecarboxylic acid to crystallization with a solvent mixture comprising a carboxylic acid and a poor solvent for 1-aminocyclopropanecarboxylic acid, the carboxylic acid having one to five carbon atoms, and the poor solvent being miscible with the organic acid.

2. The method according to claim 1, wherein the solvent mixture further comprises water.

3. The method according to claim 1, comprising the steps of:
   mixing the crude 1-aminocyclopropanecarboxylic acid with the carboxylic acid having one to five carbon atoms;
   removing insoluble matter by filtration; and
   adding the poor solvent with or without water to the filtrate to thereby crystallize 1-aminocyclopropanecarboxylic acid.

4. The method according to any one of claims 1 to 3, further comprising using acetic acid as the carboxylic acid and ethanol as the poor solvent.

5. A method for producing 1-aminocyclopropanecarboxylic acid, comprising the step of purifying a reaction product by the purification method according to claim 1, the reaction product being obtained by converting 1-carbamoylcyclopropanecarboxylic acid to 1-aminocyclopropanecarboxylic acid.

* * * * *